United States Patent
Gopalakrishnan et al.

(10) Patent No.: US 11,358,112 B2
(45) Date of Patent: Jun. 14, 2022

(54) SYSTEMS AND METHODS FOR DISPERSION OF DRY POWDERS

(71) Applicants: Ranganathan Gopalakrishnan, Germantown, TN (US); Lekhnath Pokharel, Memphis, TN (US); Rayhan Ahmed, Memphis, TN (US); Ewe Jiun Chng, Memphis, TN (US); Jason Scott Presley, Memphis, TN (US)

(72) Inventors: Ranganathan Gopalakrishnan, Germantown, TN (US); Lekhnath Pokharel, Memphis, TN (US); Rayhan Ahmed, Memphis, TN (US); Ewe Jiun Chng, Memphis, TN (US); Jason Scott Presley, Memphis, TN (US)

( * ) Notice: Subject to any disclaimer, the term of this patent is extended or adjusted under 35 U.S.C. 154(b) by 3 days.

(21) Appl. No.: 16/556,257

(22) Filed: Aug. 30, 2019

(65) Prior Publication Data
US 2020/0139336 A1    May 7, 2020

Related U.S. Application Data

(60) Provisional application No. 62/893,210, filed on Aug. 29, 2019, provisional application No. 62/724,699, filed on Aug. 30, 2018.

(51) Int. Cl.
*B01J 19/10* (2006.01)
*B01J 2/16* (2006.01)
(Continued)

(52) U.S. Cl.
CPC ............... *B01J 19/10* (2013.01); *B01J 2/16* (2013.01); *B01J 2/18* (2013.01); *B01J 4/001* (2013.01);
(Continued)

(58) Field of Classification Search
CPC ....... B01J 19/10; B01J 2/16; B01J 2/18; B01J 4/001; B01J 2208/00769; B01J 2219/1943;
(Continued)

(56) References Cited

U.S. PATENT DOCUMENTS 2,878,972 A * 3/1959 Matthews .......... G03G 15/0803
222/630
5,104,230 A * 4/1992 Douche ................. G01F 13/001
366/156.1
(Continued)

FOREIGN PATENT DOCUMENTS

| CN | 105126712 A | 12/2015 |
|---|---|---|
| GB | 1268242 A | 3/1972 |
| WO | WO2002/059574 A1 | 8/2002 |

OTHER PUBLICATIONS

International Search Report and Written Opinion, PCT/US19/048683, Gopalakrishnan, et al. (international filing date Aug. 29, 2019; WIPO Pub. Date Nov. 5, 2019)).

*Primary Examiner* — Huy Tram Nguyen
(74) *Attorney, Agent, or Firm* — Wayne Edward Ramage; Baker Donelson

(57) ABSTRACT

Systems and methods for preparing and dispersing dry powders are disclosed herein. The system includes a powder feeder, a rotating holder or disc configured to receive an input powder from the powder feeder, and one or more ultrasonic transducers. The ultrasonic transducer is configured to create standing waves, which suspend the input powder within a space above the rotating holder disc for collection and subsequent processing and/or use. Also disclosed herein is an adapter configured to fit existing off-the-shelf powder dispensers that includes an ultrasonic transducer configured to suspend an input powder in midair for collection.

14 Claims, 10 Drawing Sheets

(51) Int. Cl.
  *B01J 2/18* (2006.01)
  *B01J 4/00* (2006.01)

(52) U.S. Cl.
  CPC .............. *B01J 2208/00769* (2013.01); *B01J 2219/1943* (2013.01)

(58) Field of Classification Search
  CPC .............. A61M 11/002; A61M 11/005; A61M 2202/064
  USPC ........................................................ 366/108
  See application file for complete search history.

(56) References Cited

U.S. PATENT DOCUMENTS

| | | | |
|---|---|---|---|
| 2001/0047837 A1* | 12/2001 | Parks | B65B 1/366 |
| | | | 141/18 |
| 2002/0064400 A1 | 5/2002 | Vandewinckel et al. | |
| 2003/0111131 A1 | 6/2003 | Zhu et al. | |
| 2004/0251328 A1 | 12/2004 | Kim et al. | |

\* cited by examiner

100 # SYSTEMS AND METHODS FOR DISPERSION OF DRY POWDERS

This application claims benefit of and priority to U.S. Provisional App. No. 62/724,699, filed Aug. 30, 2018, and U.S. Provisional Appl. No. 62/893,210, filed Aug. 29, 2019, and is entitled to the benefit of those filing dates.

The complete disclosures, including the specifications, drawings and appendices, of all patents, patent applications, and publications cited herein, including U.S. Provisional App. No. 62/724,699, U.S. Provisional App. No. 62/893,210, U.S. application Ser. No. 11/381,952 (US Pub. 2006/0249144), and U.S. Pat. No. 8,875,702, are hereby incorporated in their entireties by specific reference for all purposes.

FIELD OF THE INVENTION

The present invention relates generally to improved systems and methods of aerosol dispersion of dry powders. More particularly, disclosed herein are systems and methods for preparation and dispersion of dry powder at high concentrations with particles in the micron or nanometer size range using ultrasonic waves.

BACKGROUND OF THE INVENTION

Dispersion of dry powders as aerosols is a technique employed in manufacturing, medical and environmental technologies, agriculture, and many other fields. Current aerosol dispersion methods and devices can reliably produce aerosol particles as small as 100 nanometers at varying concentrations. Many fields require aerosols at concentrations of over 5,000 particles per cubic centimeter. However, currently technologies struggle with producing high-concentration aerosol powder over sustained periods, particularly when applications require particles with diameters in the nanometer and micron range.

A significant issue with dispersing powders containing particles that are micrometer or nanometer-sized is their cohesive nature. Nanoparticles and microparticles have a very large surface area to volume ratio, resulting in high surface energy that creates a tendency of nanoparticles and microparticles to agglomerate. Thus, the smaller the particles, the greater the propensity for the particles to bind together and the greater the dispersion force required to separate the particles from one another. Overcoming the forces that tend to keep agglomerated nanoparticles together represents a significant hurdle for dispersion of dry powders.

Current technology designed to separate agglomerated particles typically relies on a venturi tube to create a turbulent flow and shear forces through the convergence of differential air velocities. In such technologies, the air velocity through the venturi tube greatly exceeds the velocity of the air approaching the tube. Therefore, as particles are pulled into the venturi, shear forces are created when the two air flows meet, which can dissociate agglomerated particles from one another.

Certain technologies employ a turn table or rotating disc, a capillary tube, or a venturi throat to further accentuate the difference in air velocities. However, the introduction of additional elements or moving parts can create confounding problems with agglomeration. In addition to cohesion with one another, nano/micro powders tend to adhere to surfaces of walls and moving parts while being dispersed. This can cause a problem as dry particles are pulled through various parts of a particle dispersion system, particularly when feeding powder into a venturi tube. For instance, dispersion technologies that employ a capillary tube struggle with agglomeration. In such systems, the particles often clog the capillary, which causes a steady drop in concentration of dispersed aerosol particles over time. In many technologies that incorporate multiple parts, there is a burst of particle concentration at the beginning of the dispersion followed by a slow decay and eventual stoppage of particle generation. This burst followed by a decrease in concentration of dry particles within the aerosol occurs because, initially, particles are relatively easily removed from the surface by mechanical or fluid dynamic forces. However, as time progresses, particles that are highly cohesive or difficult to remove create a powder bed, which makes sustained particle generation difficult. This causes "caking" or formation of a semi-rigid mass of powder over a short time. Thus, current mechanisms for dispersing dry powder that require multiple moving parts are not reliable in producing high concentrations of small particles over a sustained period.

To overcome the problem of "caking," the number of moving parts required for introducing powder into a venturi tube should be reduced, and the overall all process for powder dispersion requires simplification. Thus, there is a need for a powder dispersion system capable of generating aerosol nanoparticles of cohesive powders at high concentrations for long periods of time.

SUMMARY OF THE INVENTION

In various exemplary embodiments, systems and methods for the ultrasonic production of fine particles for dispersion as aerosol are presently disclosed. The presently disclosed embodiments are configured to produce stable, high concentrations of aerosol particles at a wide range of sizes. Embodiments are configured to produce nano/micro particles from cohesive powders. In embodiments, the system and methods produce a steady and high concentration of aerosol particles for more than one hour. In on embodiment, the system is configured to produce particles that comprise a diameter of less than 10 micrometers. Other objects and advantages of this invention will become readily apparent from the ensuing description.

DETAILED DESCRIPTION OF EXEMPLARY EMBODIMENTS

Figure 1:
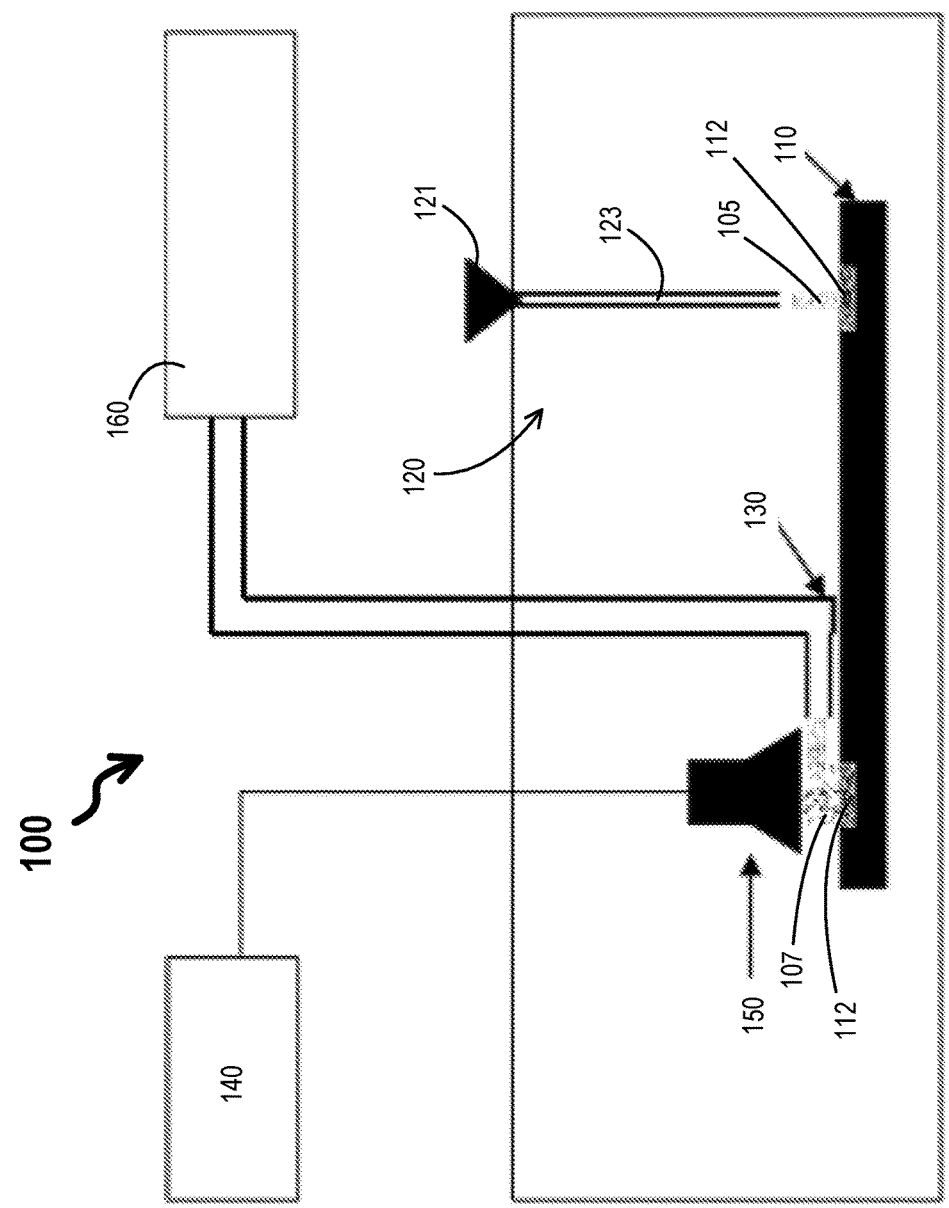
FIG. 1 is a schematic cross-sectional, side view of a system for preparing aerosol dry powders for dispersion, under one embodiment. The system is shown equipped with an ultrasonic generator and ultrasonic transducer.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a," "an," and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function The terms "comprising" and "including" and "having" and "involving" (and similarly "comprises," "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or "in the region of." When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

In various exemplary embodiments, the present invention comprises a system for dry powder dispersion. The system can be configured to produce dry powder as aerosol in the micron to nanometer size range without the use of moving parts. Embodiments employ ultrasonic energy to disperse dry-powder particles for further de-agglomeration. The system comprises at least one ultrasonic transducer configured to produce fine particles of cohesive powders for continuous dispersion at stable, high concentrations over extended time periods.

Aerosolization of dry powders can be viewed as a two-step process: The first step is the separation of the interfacial contact between powder particles and the surface on which they are resting (wall of process equipment or other particles). This requires that sufficient mechanical energy greater than the energy of adhesion for a given powder be supplied. The adhesion energy of powder particles follows a distribution that is affected by the material properties and the particle size distribution. For any quantum of mechanical energy applied to disperse a powder, particles with adhesion energy less than the applied energy will be dispersed while those with adhesion energy greater than the applied energy will not be dispersed. As time progresses, more and more of the easily dispersible particles are removed and mixed with the gas flow, leaving behind powder mass that is composed of highly adherent particles, thus making the sustained generation of particles at constant number concentration challenging. The second step in the aerosolization of dry powders is breaking up of the agglomerates of particles to form aerosols in the sub-micron size range from nanostructured, agglomerated powders. Again, the adhesion between primary particles of the powder scales with inverse size leading to high adhesion energy of the nano-agglomerates. The most convenient way to apply mechanical energy to break up the agglomerates is through turbulent kinetic energy of a gas and particle-wall collisions. Depending on the magnitude of the impact forces exerted on the particles, various degrees of de-agglomeration is likely to take place. Detaching powder particles down to individual particles is extremely difficult, as it requires a high amount of mechanical energy to overcome the inter-particle adhesion energy.

FIG. 1 shows a schematic view of a system 100 for ultrasonic production and dispersion of cohesive powders under one embodiment of the present invention. This system comprises a rotating disc 110 that receives a powder to be dispersed 105. A powder feeder 120 may be used to introduce the powder to be dispersed 105 into the system. The system further comprises an ultrasonic generator 140 coupled to an ultrasonic transducer 150. The system 100 may further include a sampling probe 130 and a de-agglomeration setup 160.

In several embodiments, the rotating disc 110 comprises a groove 112 configured to receive and hold the powder to be dispersed 105. In embodiments, the groove 112 forms a continuous circle within a top face of the rotating disc 110 and extends partially through the rotating disc 110. The rotating disc 110 can be comprised of any material suitable for receiving powder. In embodiments, the rotating disc is comprised of metal. The rotating disc can be comprised of an aluminum alloy. In one embodiment, the disc 110 comprises a 6000 series aluminum alloy. The aluminum alloy may comprise Aluminum 6061. The rotating disc 110 may be any of various sizes depending on the aerosol dispersion requirements. In portable embodiments, the disc 110 is about 10 mm thick and comprises a radius of about 140 mm. In one embodiment, the groove is about 10 mm wide and comprises a depth of about 2 mm.

The powder feeder system 120 is configured to introduce powder 105 directly into the groove of the rotating disc 110. The powder feeder system 120 may comprise a funnel 121 for receiving and holding input powder. The powder feeder system may further comprise a distribution channel or tube 123. The funnel 121 and the distribution channel or tube 123 may be integral to one another or reversibly linked together. The feeder system 120 may further comprise one or more vibrating motors configured to agitate the funnel 123 of the feeder system 120. The one or more vibrating motors may comprise a rotational speed of about 10,000-15,000 rpm. Certain embodiments comprise up to four vibrating motors.

The funnel may comprise a mesh strainer configured to prevent particle clusters over a given size or diameter from passing into the distribution channel 123. In embodiments, the strainer allows only particles that are about 1 mm in diameter or less to enter the distribution channel or tube 123. The mesh strainer may be further configured to agitate large clusters of powder such that the clusters are broken down to a sufficiently small size to pass therethrough. An opening of the distribution channel or tube 123 of powder feeder system 120 may be disposed over the groove in the rotating disc 110 for distribution of input powder therein. In operation, the disc 110 slowly rotates about an axis such that the groove continuously receives the powder to be dispersed 105 from a powder feeder system 120. The disc 110 can be configured to rotate at a speed from about 2 rpms to 10 rpm.

The at least one ultrasonic transducer 150 can be placed anywhere along or above the rotating disc. In several embodiments, the ultrasonic transducer 150 is suspended above the groove 112 of the rotating disc 110 in a location that is distinct from the feeder system distribution channel 123. As seen in FIG. 1, the ultrasonic transducer may be located approximately opposite the feeder system distribution channel.

The ultrasonic transducer 150 is configured to create a resonant ultrasonic frequency and a resultant standing wave pattern from pressure waves in the air column between the transducer 150 and the rotating disc 110. In operation, these ultrasonic waves agitate the input powder 105 within the groove 112 of the rotating disc 110 to create standing waves manifested by levitation of the input powder 105. When the transducer 150 is suspended above the rotating disc 110, the distance between the ultrasonic transducer 150 and the rotating disc 110 can be adjusted to achieve the desired levitation of the input powder 105. In embodiments, optimal levitation is achieved when the ultrasonic transducer 150 is between about 2 to 10 mm above the rotating disc 110. Thus, as the rotating disc 110 rotates about its axis, the input powder 105 within the portion of the groove 112 below the ultrasonic transducer 150 forms an isolated, dense dust cloud of aerosol particles 107 suspended within the space between the rotating disc 110 and the ultrasonic transducer 150.

As can be seen, when so suspended, the aerosol particles 107 have no physical contact with any of the moving parts of the system before being sampled and removed for further de-agglomeration (as discussed below). This lack of physical contact with the system reduces the accumulation of powder on the surfaces of the system and prevents "caking" to ensure sustained production of high-concentration aerosol particles over long periods of time. This application is particularly advantageous for use with cohesive input powders.

As shown in FIG. 1, a sampling probe 130 can be configured to extract a sample of the suspended aerosol 107 between the transducer 150 and the rotating disc 110 for analysis. In various embodiments, the sampling probe 130 is configured to determine the size of fine-particle powders produced from the application of ultrasonic energy as described herein. The sampling probe can be connected to a vacuum generator to produce a negative pressure for procurement of aerosol to be sampled.

After ultrasonic excitation and resultant levitation, the aerosol particles 107 can be directed to the de-agglomeration setup or system 160 for further particle separation. Embodiments comprise a vacuum generator configured to create a negative pressure that directs the aerosol particles 107 to the de-agglomeration setup 160. In several embodiments, the de-agglomeration setup 160 comprises a low intensity vacuum or a high intensity vacuum. In some embodiments, a high intensity vacuum comprises more than one venturi acting in tandem with one another. An exemplary low-intensity vacuum comprises a TDSS series air-operated vacuum pump (available from Air-Vac Engineering Company—Seymour, Conn.), and an exemplary high intensity vacuum comprises an Ultra-Vac Series air-operated vacuum pump (available from Air-Vac Engineering Company—Seymour, Conn.). The sampling probe 130 can also be connected to the vacuum generator used in the de-agglomeration setup.

In embodiments, the de-agglomeration setup 160 comprises a venturi tube to create shear forces configured to dissociate agglomerated particles from one another.

Also disclosed is a method to increase the efficiency of a dry powder disperser using the ultrasonic transducer described herein. The method includes equipping a dry powder disperser with an ultrasonic transducer and permitting the transducer to levitate an input powder for collection by a de-agglomeration setup.

In several embodiments, the present invention may comprise an adapter configured to be utilized with off-the-shelf powder dispersers. The adapter comprises an ultrasonic transducer configured to prepare an input powder for de-agglomeration. The ultrasonic transducer can be configured to suspend the input powder such that the powder has no physical contact with any surface before being collected for de-agglomeration.

In various embodiments described herein, the ultrasonic transducer 150 can be configured to produce any frequency in the ultrasonic range. In embodiments the ultrasonic transducer produces sound waves with frequencies of about 20 kHz or more. The ultrasonic transducer may be configured to produce sound wave frequencies of about 20 kHz to 200 kHz. In several embodiments, the ultrasonic transducer 150 is powered by an ultrasonic generator 140.

The systems and methods described herein permit the production of a steady and high concentration of aerosol particles for up to 10 hours, 7 hours, 5 hours, 3 hours, or 1 hour. The system can disperse stable concentrations of dry particles for up to 2 hours. In certain embodiments, the system disperses dry-particle powders for about 1.5 hours. By way of nonlimiting example, the device may be configured for use in various aerosol based additive manufacturing, powder processing, inhalation and dosimetric studies, to name a few applications.

The cloud of aerosol 107 formed from ultrasonic excitation of the input powder 105 may comprise any commercially useful particle size. The aerosol may comprise particles in the nanomolecular size range. Particles may be produced that are smaller than 100 nm. Particles can be less than 100 microns in size. The aerosol 107 may comprise particles as small as 10 microns in size. In certain embodiments, the aerosol particles 107 are less than 10 microns in size. Aerosol particles with diameters as small as 0.1 microns, 0.5 microns, 1 micron, 2 microns, 3 microns, 4 microns, 5 microns, 6 microns, 7 microns, 8 microns, 9 microns, or 10 microns may be produced through the presently disclosed systems and methods. The systems and methods described herein can produce particles between about 0.1 to 0.5 microns in size. Particles that are smaller than 0.1 microns in size also may be produced.

The systems and methods disclosed herein are capable of producing high-concentration aerosols. Several embodiments produce aerosols at concentrations up to about 1,000,000 particles per cubic centimeter. The systems and methods disclosed herein may produce maximum concentrations of aerosols that range from about 5,000 particles per cubic centimeter to up to about 1,000,000 particles per cubic centimeter. In embodiments, the present systems and methods produce aerosol concentrations of between about 5,000 particles per cubic centimeter up to about 50,000 particles per cubic centimeter. Aerosols comprising concentrations of about 10,000 particles per cubic centimeter can be generated through the present systems and methods. The concentration of the aerosol particles can be directly proportional to the number of ultrasonic transducers operating within the disclosed system. In embodiments, increasing the number of ultrasonic transducers increases the maximum aerosol concentration production capacity of the systems and methods disclosed herein.

Embodiments of the presently disclosed systems and methods are suitable for aerosolizing any commercially useful material, including, but not limited to, carbonaceous materials (e.g. carbon nanotubes), metal oxides, amorphous materials, and other materials known in the art of powder particle dispersion. The systems and methods herein also may be used to disperse materials including, but not limited to, ceramic materials, pollen or agricultural dust, radioactive material, and pharmaceutical powders. Certain embodiments are particularly useful for the creation and aerosol dispersion of cohesive powders including, but not limited to, polyimide powders, titanium dioxide, calcium phosphate, silicon carbide, barium titanate, lead zirconate titanate, hydroxyapatite, ferrous oxide, and other powders with strong cohesive tendencies.

FIGS. 2A-B show a top view and cross-sectional view (from a front angle of 45 degrees to the right) of another embodiment of an ultrasonic aerosol generator in accordance with the present invention. A powder feeder channel or tube 223 introduces powder to be disbursed 205 to a brush 225 above a rotating circular holder, disk or table 210. Rotation is provided by a motor, such as a DC motor 214. The powder is spread along the surface of the holder by action of the brush as the holder rotates. The powder then passes under a number of ultrasonic transducers 250a-c suspended above the holder, which agitate the input powder 205 as it passes below each transducer to achieve the desired levitation of the input powder, as described above. The apparatus may comprise a housing 290 encompassing the rotatable holder, and a gas inlet 270 configured to introduce gas into the housing. This results in multiple or distributed clouds of aerosol particles, which mix with the gas flow from the gas inlet 270, and then are removed from the apparatus through an aerosol outlet 230. In the figure shown, the aerosol outlet is positioned between the multiple transducers, and may be positioned equi-distant therefrom. The brush achieves greater spead and more even dispersement of the powder on the surface, which enhances the creation of the suspended particle clouds from the multiple transducers, and thus the production of a steady and high concentration of aerosol particles, particularly nanoparticles, for a sustained period of time.

Figure 2:
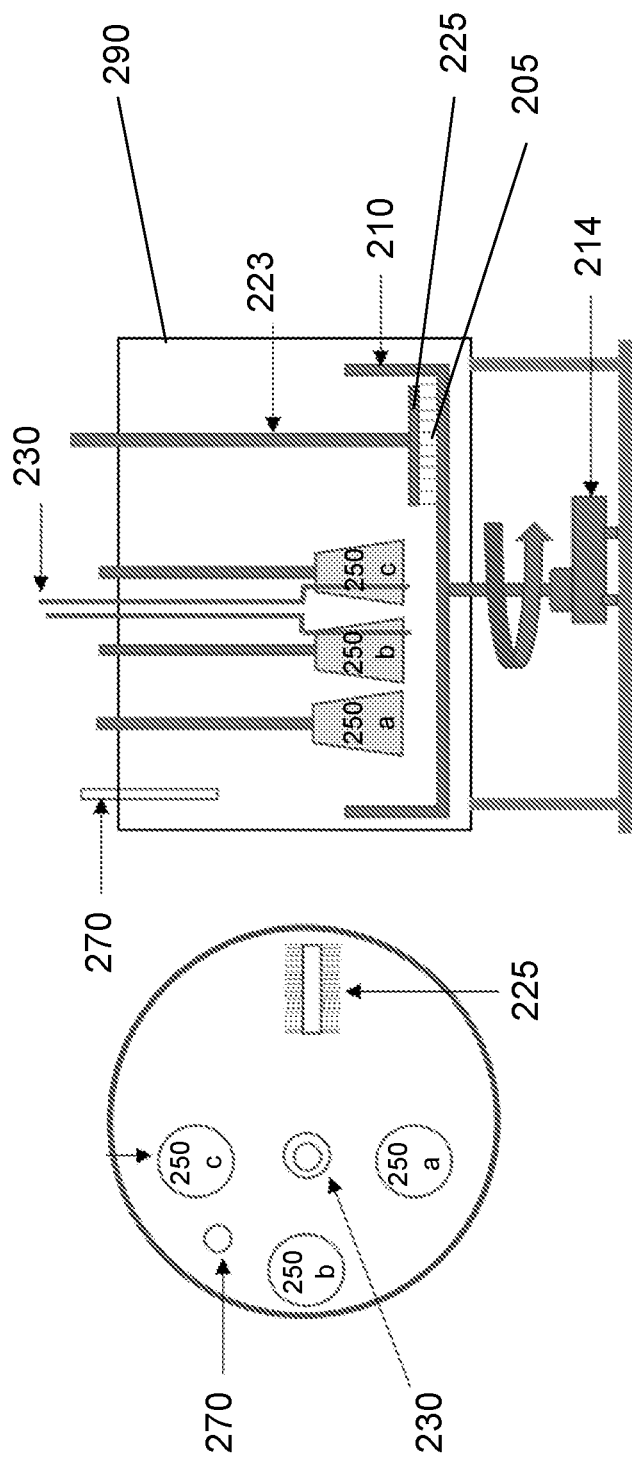
FIGS. 2A-B show a top view and front cross-sectional view of another embodiment of an ultrasonic aerosol generator.
Figure 3:
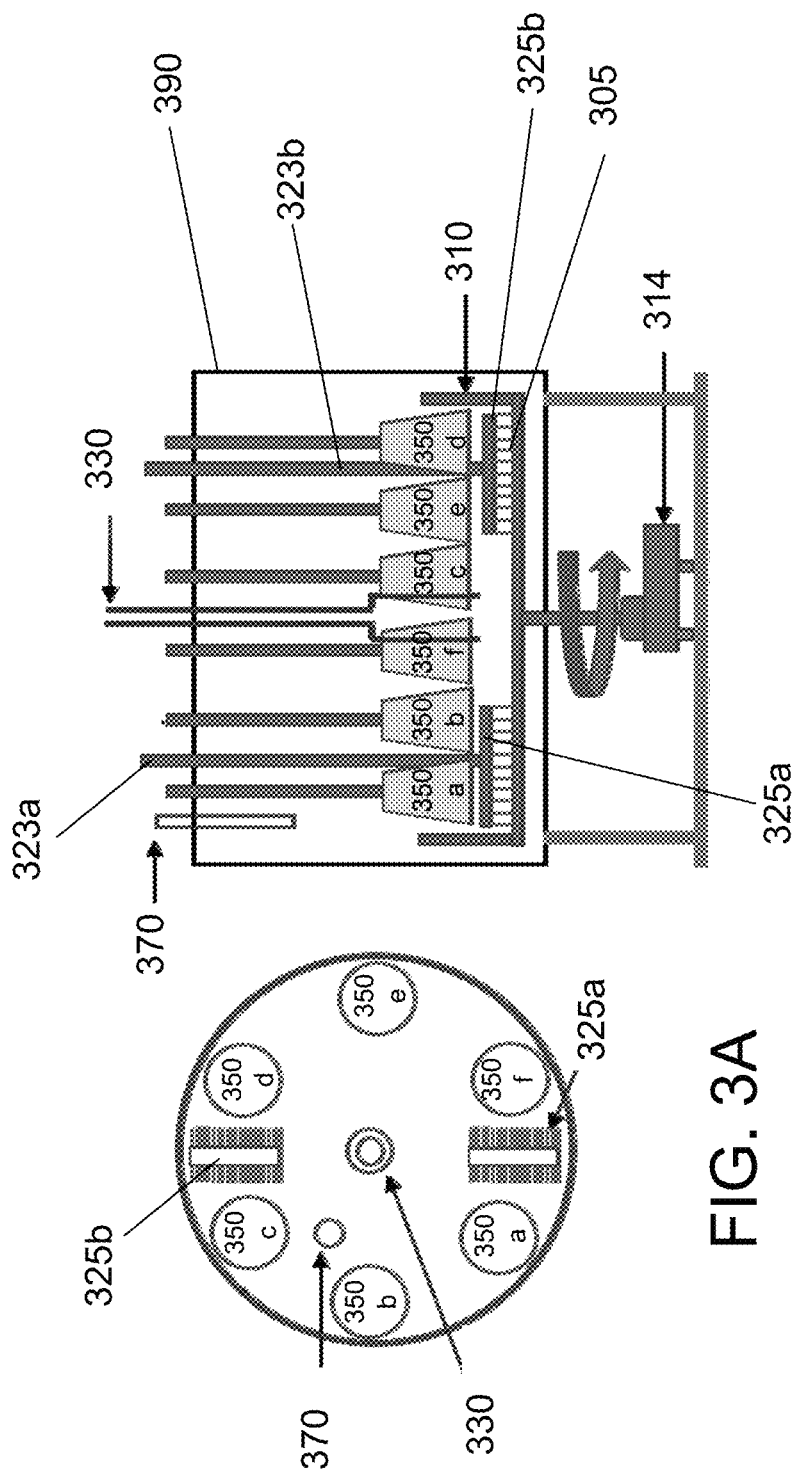
FIGS. 3A-B show a top view and front cross-sectional view of another alternative embodiment of an ultrasonic aerosol generator.

FIGS. 3A-B show an enhanced version and similar views of the generator of FIGS. 2A-B. Two powder feeder channels or tubes 323a, b introduces powder to be disbursed 305 to a corresponding brush 325a, b above a rotating circular holder, disk or table 310. Rotation is provided by a motor, such as a DC motor 314. The powder is spread along the surface of the holder by action of the brush as the holder rotates. The powder then passes under a number of ultrasonic transducers 350a-f suspended above the holder, which agitate the input powder 305 as it passes below each transducer to achieve the desired levitation of the input powder, as described above. The apparatus may comprise a housing 390 encompassing the rotatable holder, and a gas inlet 270 configured to introduce gas into the housing. This results in multiple or distributed clouds of aerosol particles, which mix with the gas flow from the gas inlet 370, and then are removed from the apparatus through an aerosol outlet 330. In the figure shown, the aerosol outlet is positioned between the multiple transducers, and may be positioned equi-distant therefrom. Similarly, the transducers may be evenly spaced around the holder. The brush achieves greater spead and more even dispersement of the powder on the surface, which enhances the creation of the suspended particle clouds from the multiple transducers, and thus the production of a steady and high concentration of aerosol particles, particularly nanoparticles, for a sustained period of time.

Figure 4:
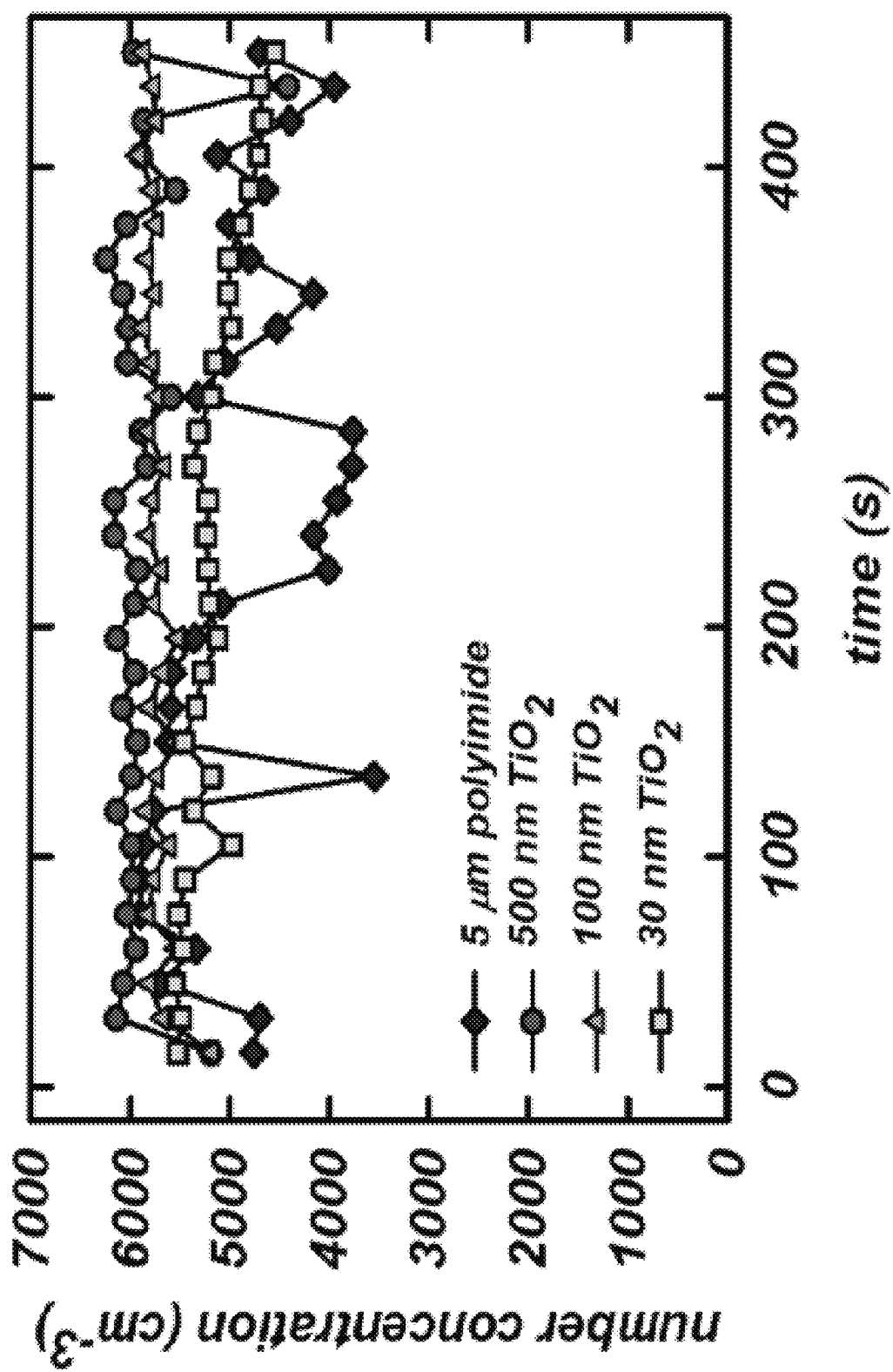
FIG. 4 is a graphical representation showing the stable production of fine aerosol particles at a high concentration over time from different cohesive powders or gasses using the presently disclosed system.
Figure 5A:
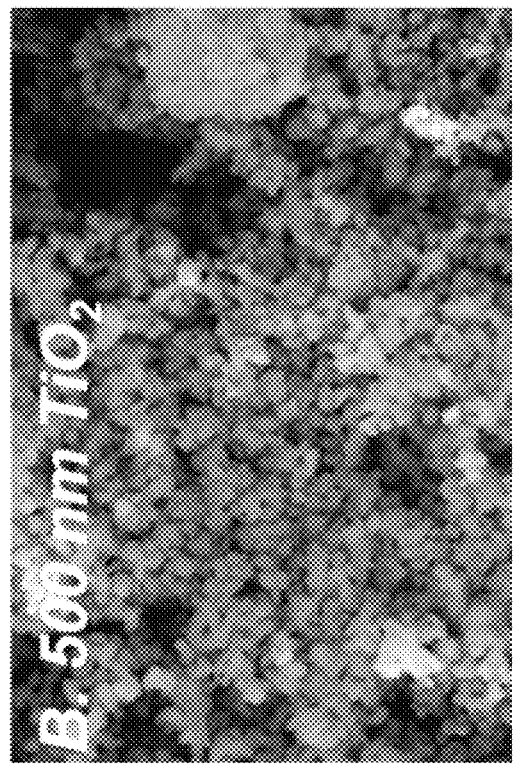
FIGS. 5A-D show scanning electron microscopy (SEM) images of various particles and sizes in a native powder form.
Figure 5B:
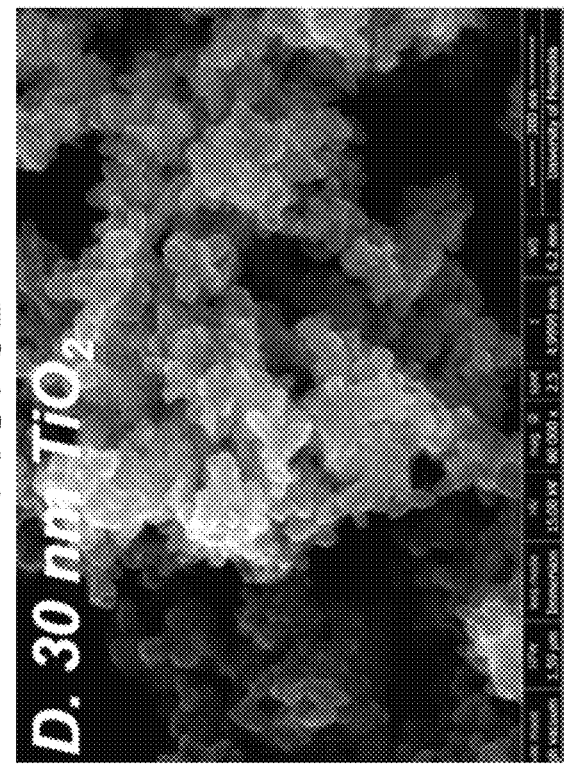
Figure 5C:
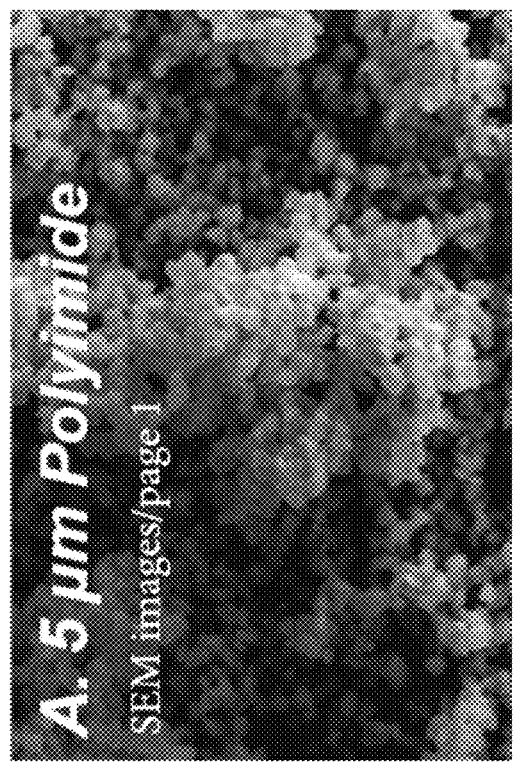
Figure 5D:
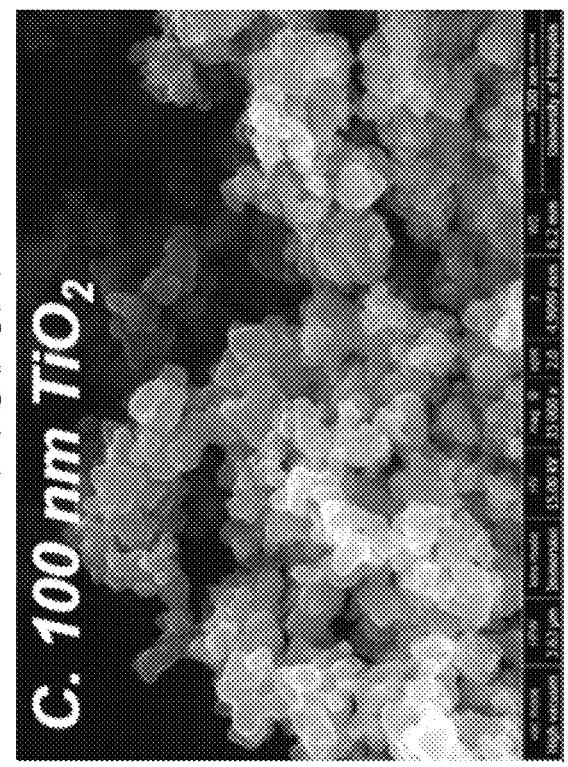
Figure 6B:
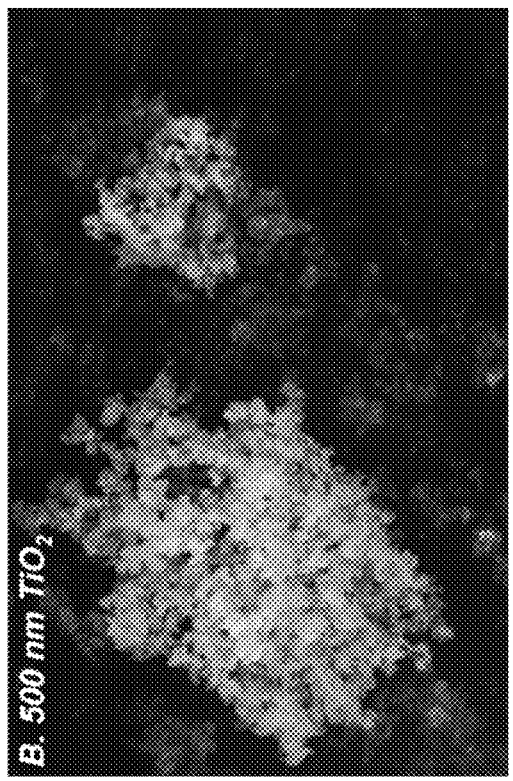
FIGS. 6A-D show SEM images of various particles and sizes collected from the gas phase after aerosolization via the systems and methods described herein.
Figure 6D:
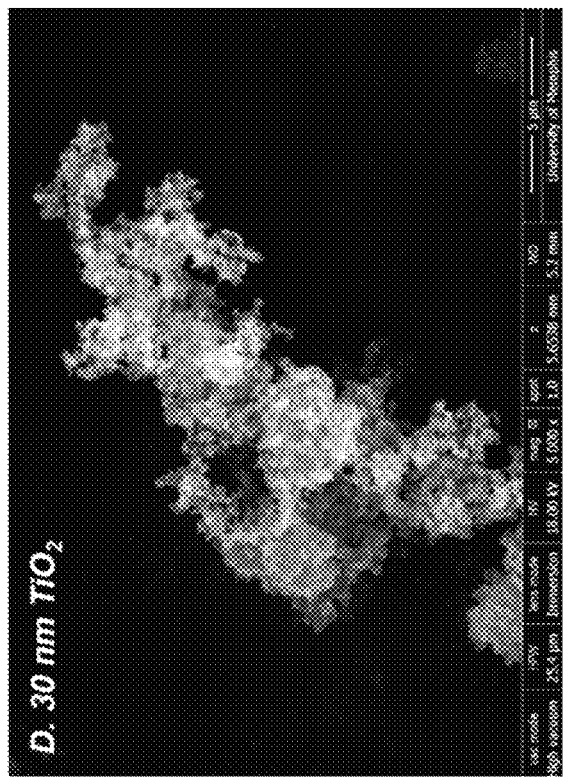
Figure 6A:
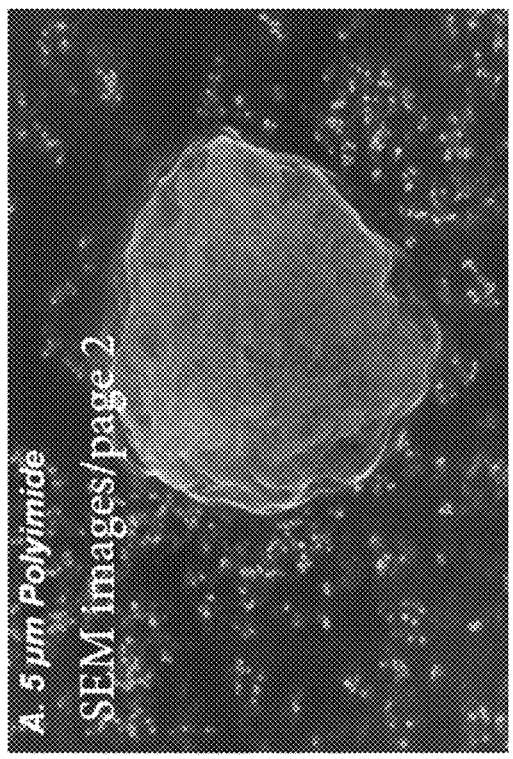
Figure 6C:
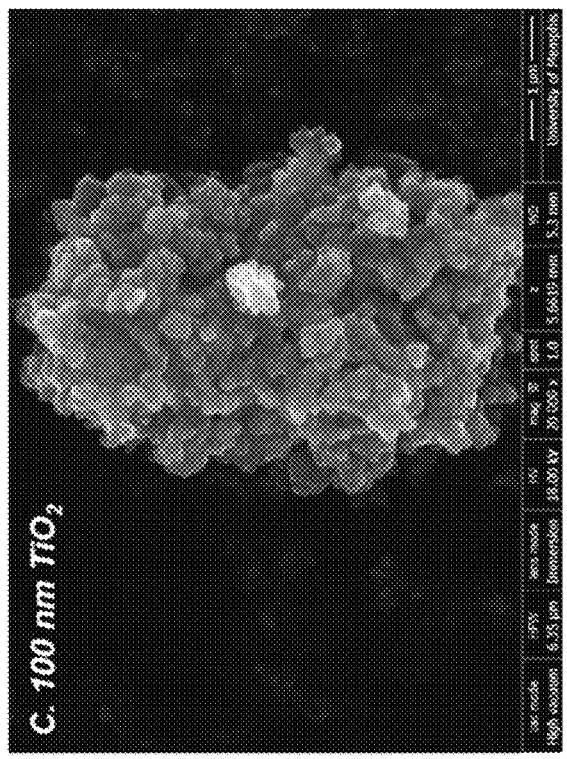

FIG. 4 shows a graphical representation of experimental data obtained after dispersion. The concentration of two cohesive powders of various sizes ranging from 5 microns to 500 nm (denoting the primary particle size) was randomly sampled from a 450-second window of time during a measurement period that lasted about 30 minutes. The data were obtained using 5 μm polyamide powder and rutile titanium dioxide ($TiO_2$) powders of 500 nm, 100 nm, and 30 nm mean size of primary input particles. The reported concentration represents dispersed particles in the 0.3-10 mm range. As shown in FIG. 2, the systems and methods described herein produced stable concentrations of $TiO_2$ for all particle sizes and for 5 μm polyimide particles. These data confirm that the systems and methods disclosed herein can consistently aerosolize a wide range of particles and particle sizes, including low density materials to high density metal oxides, at highly stable and tunable concentrations over extended periods of time.

Figure 7A:
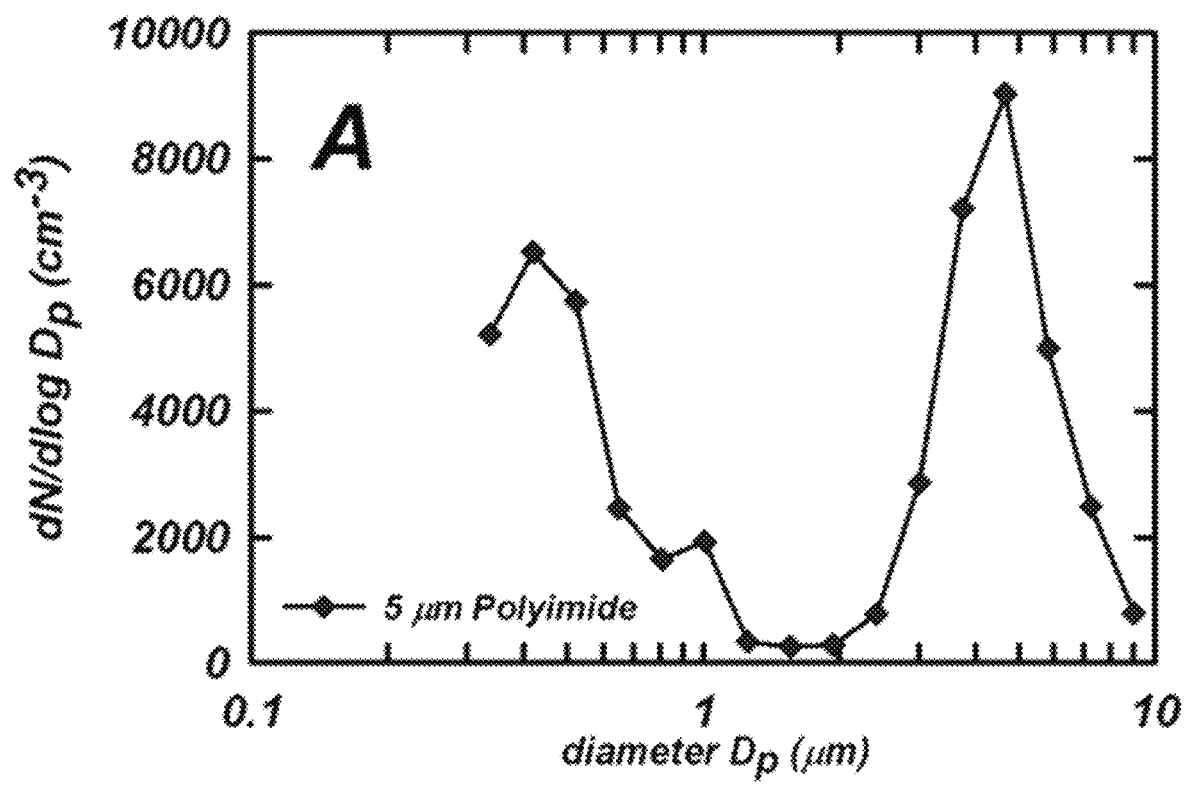
FIGS. 7A-B provide the size distribution of (A) 5 µm Polyimide, and (B) 500 nm, 200 nm, and 30 nm TiO$_2$ aerosol particles obtained using an Optical Particle Sizer (OPS) after de-agglomeration via a low-intensity venturi pump.
Figure 7B:
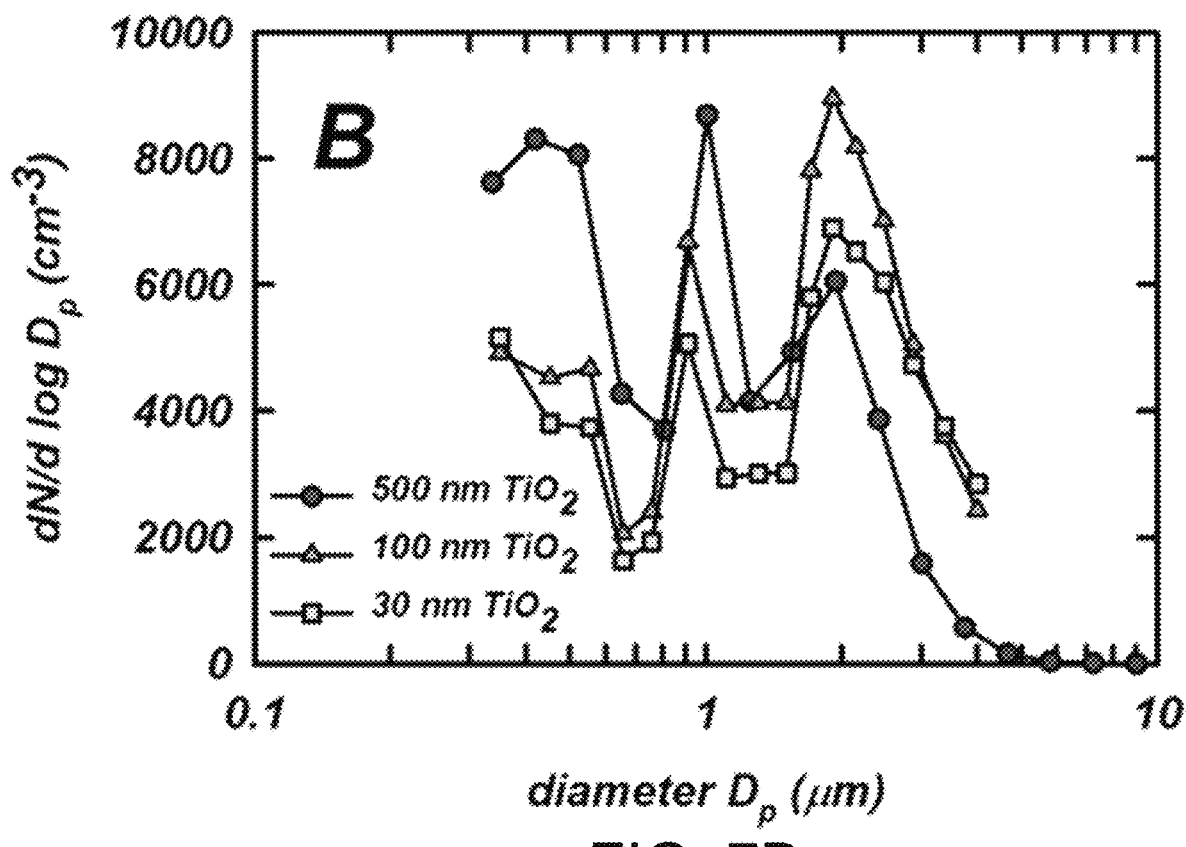
Figure 8A:
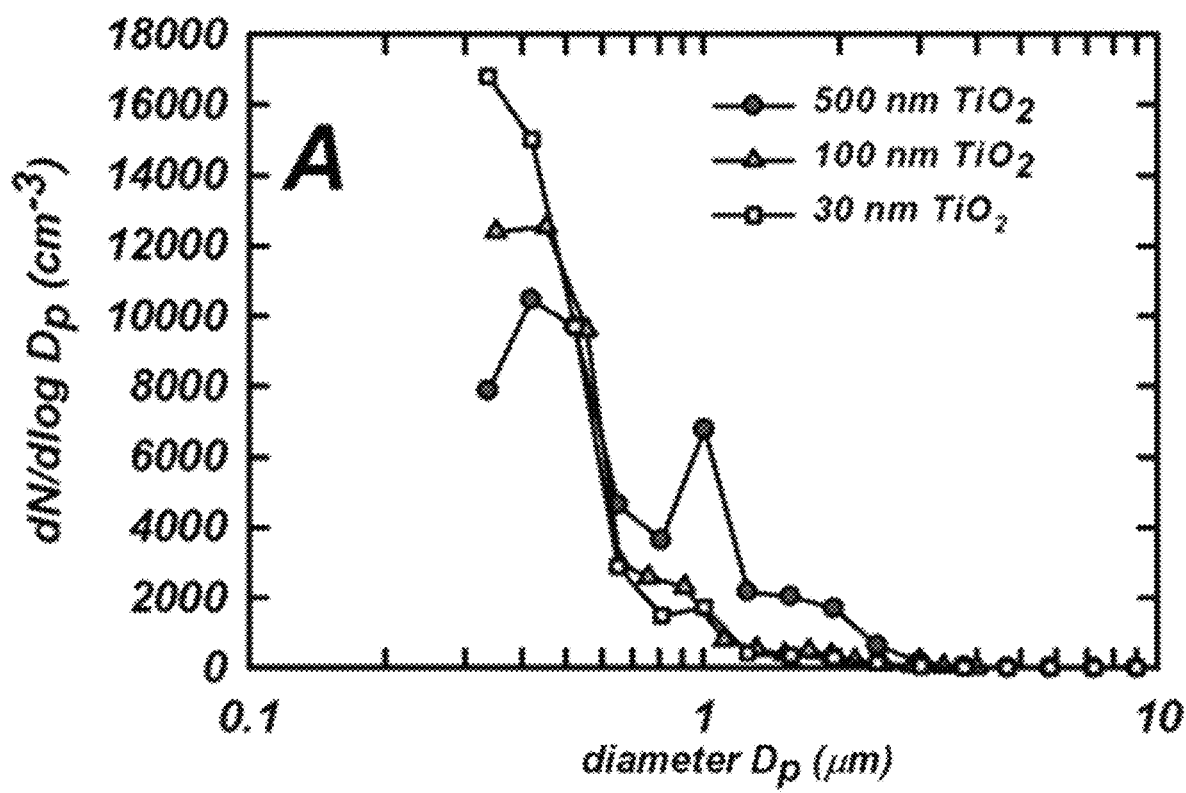
FIGS. 8A-B provide the size distribution of particles de-agglomerated using a high-intensity venturi pump using (A) an OPS; and (B) an Electrical Mobility Analysis (DMA).
Figure 8B:
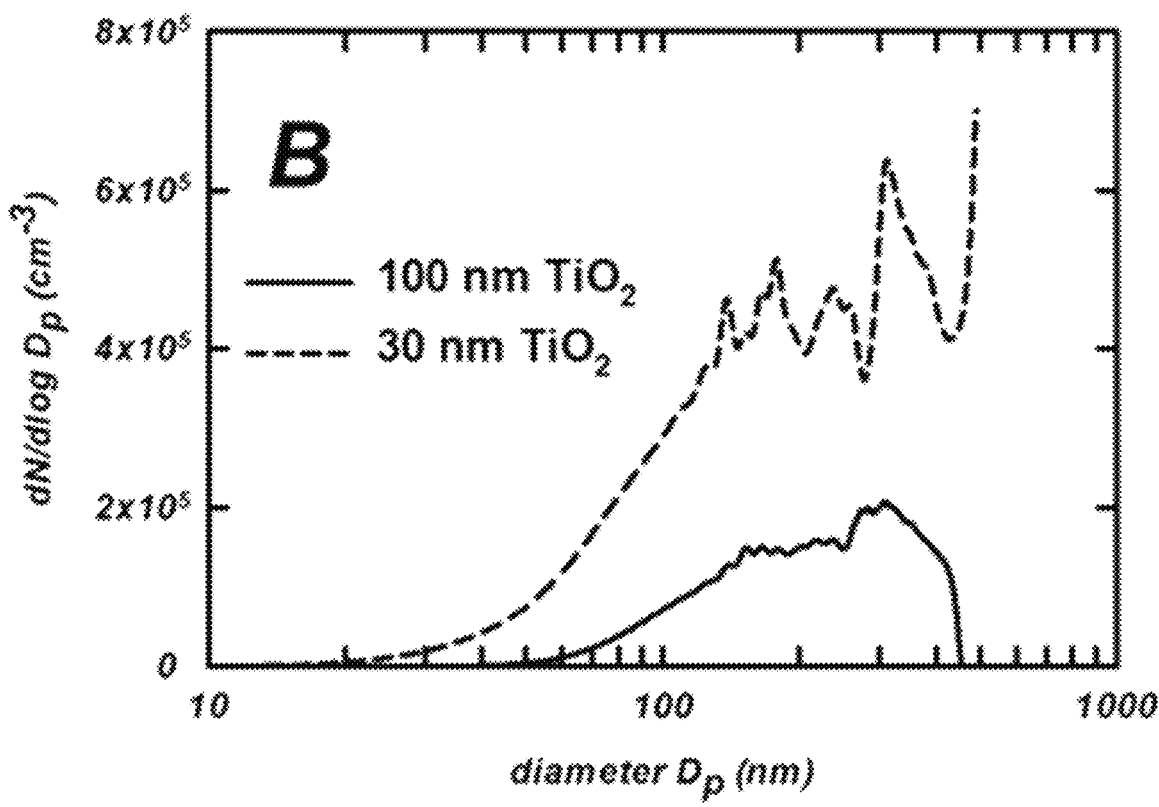
Figure 9A:
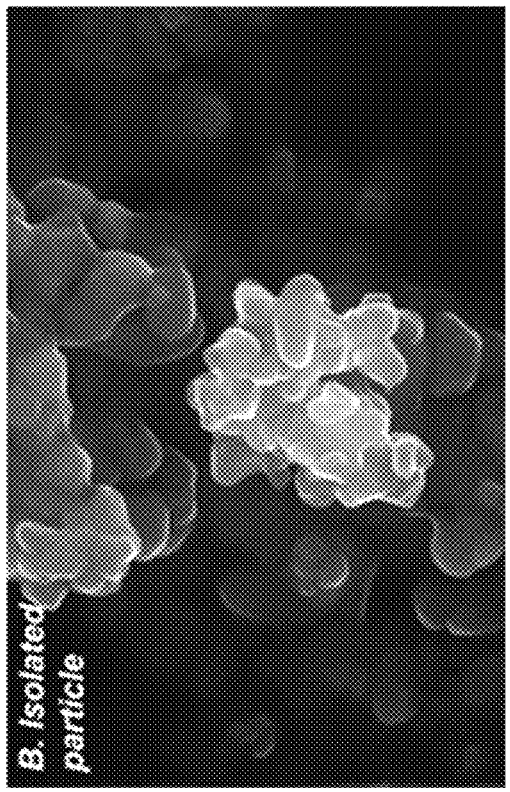
FIGS. 9A-D show SEM images of particles collected downstream of the DMA for 100 nm $TiO_2$ aerosol particles after de-agglomeration with a high-intensity venturi pump.
Figure 9B:
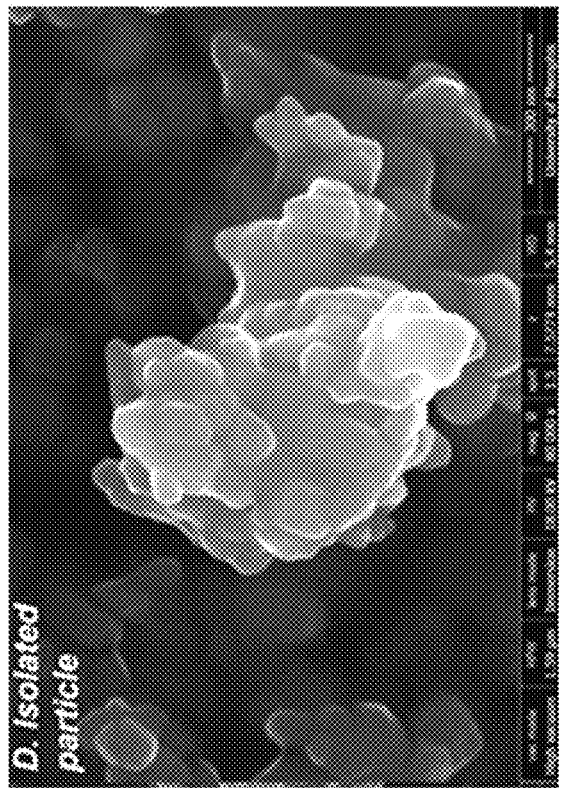
Figure 9C:
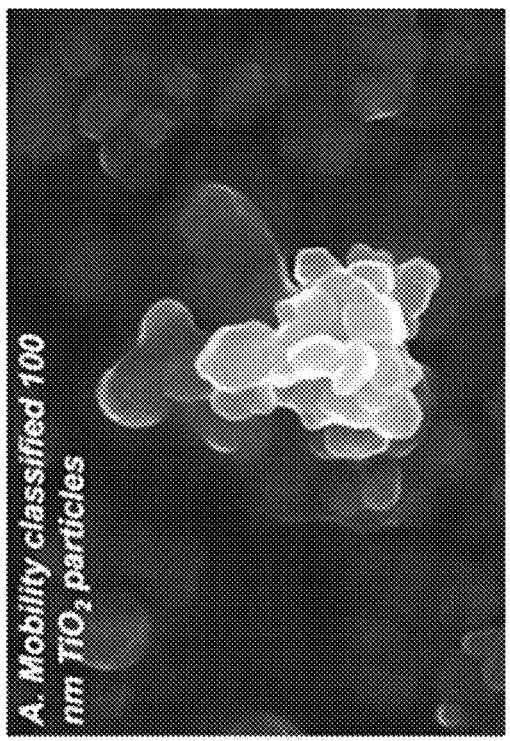
Figure 9D:
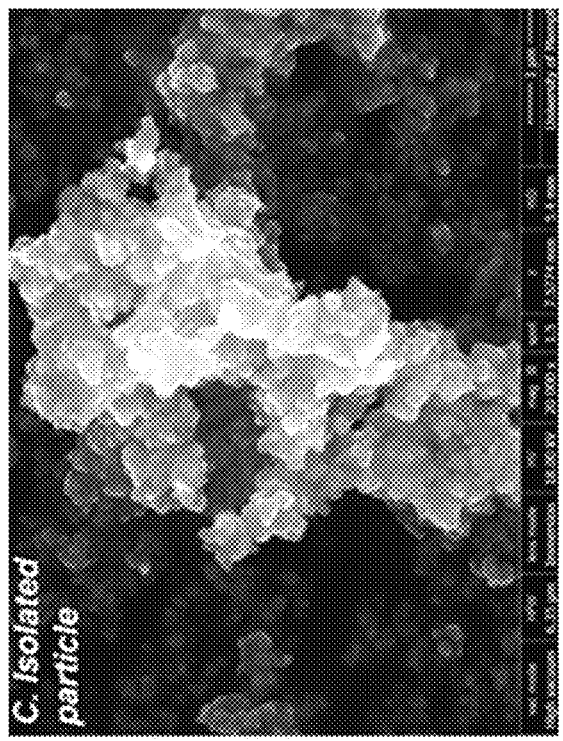
Figure 10A:
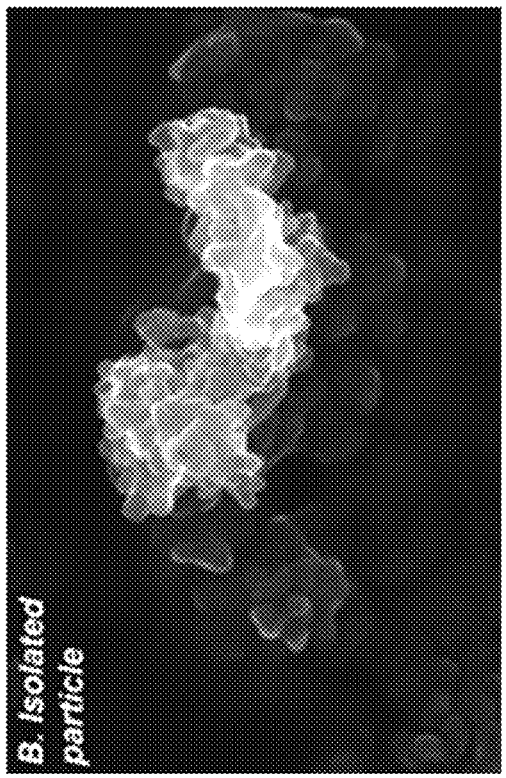
FIGS. 10A-D show SEM images of particles collected downstream of the DMA for 30 nm $TiO_2$ aerosol particles after de-agglomeration with a high-intensity venturi pump.
Figure 10B:
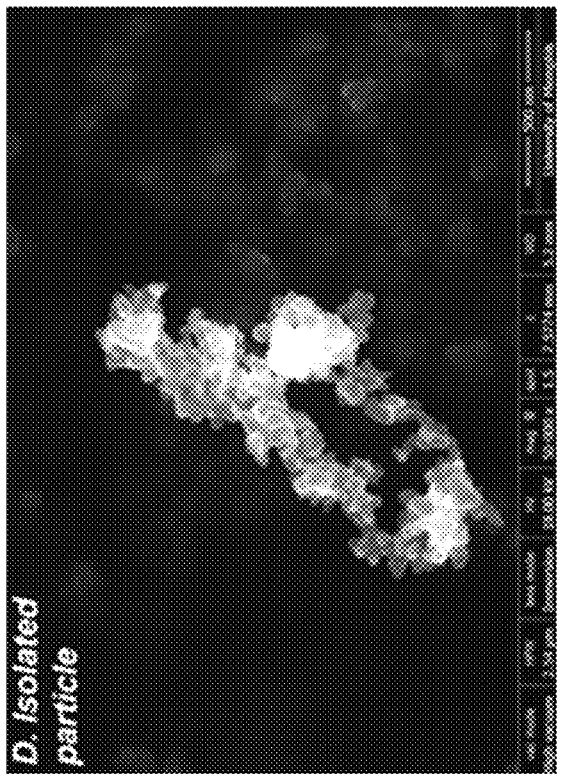
Figure 10C:
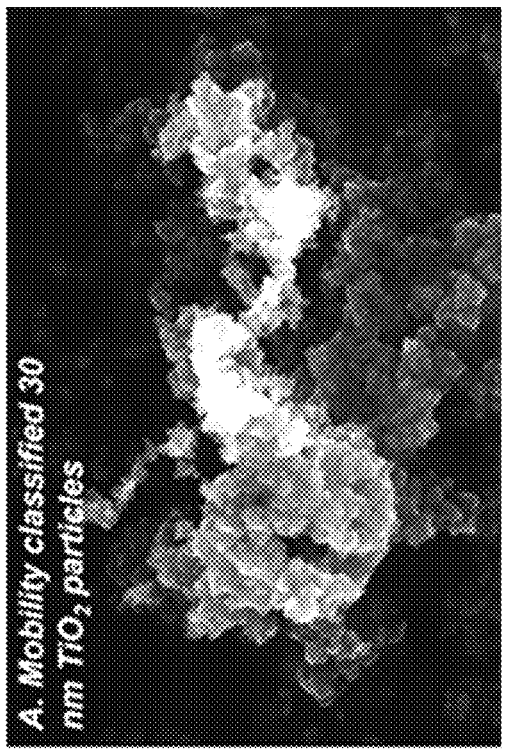
Figure 10D:
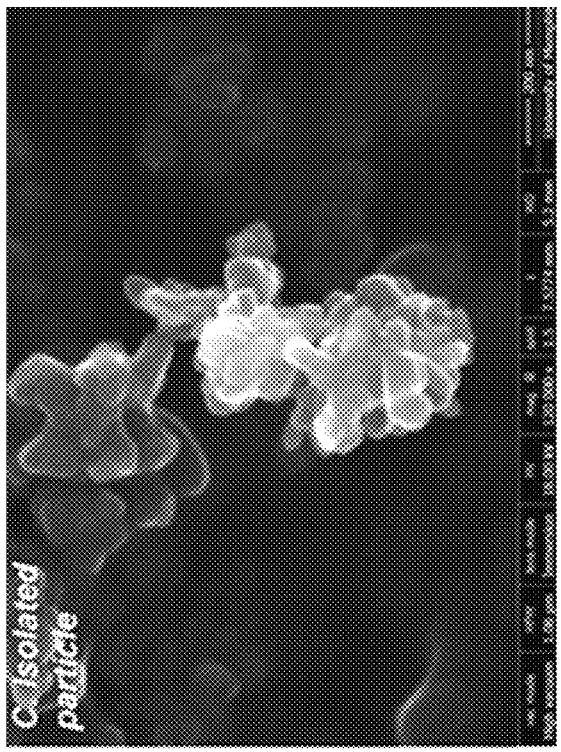

FIGS. 5A-D and 6A-D show SEM images of polyimide and $TiO_2$ particles of various sizes in their native powder state and those collected in the gas state after dispersion using the systems and methods described herein. As can be seen, the particles collected following dispersion (FIG. 6) showed significantly less agglomeration than those shown in the native powder state (FIG. 5). FIGS. 7A-B show the size distribution of (A) 5 μm Polyimide, and (B) 500 nm, 200 nm, and 30 nm $TiO_2$ aerosol particles obtained using an Optical Particle Sizer (OPS) after de-agglomeration via a low-intensity venturi pump. FIGS. 8A-B show the size distribution of particles de-agglomerated using a high-intensity venturi pump using (A) an OPS; and (B) an Electrical Mobility Analysis (DMA). FIGS. 9A-D show SEM images of particles collected downstream of the DMA for 100 nm $TiO_2$ aerosol particles after de-agglomeration with a high-intensity venturi pump. FIGS. 10A-D show SEM images of particles collected downstream of the DMA for 30 nm $TiO_2$ aerosol particles after de-agglomeration with a high-intensity venturi pump.

In various exemplary embodiments, the presently disclosed subject matter comprises systems and methods employing a novel dry powder dispersion mechanism to ensure that powder is continuously fed into a de-agglomeration setup at high, stable concentrations over time. The systems and methods disclosed herein can be scaled to produce cohesive-powder aerosols at a wide range of concentrations and sizes.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art. Those skilled in the art will recognize, or be able to ascertain, using no more than routine experimentation, numerous equivalents to the specific substances and procedures described herein. Such equivalents are considered to be within the scope of this invention, and are covered by the following sample representative claims.

What is claimed is:

1. A system for preparing dry powders for dispersion, comprising:
    a rotatable holder configured to receive an input powder;
    a powder feeder tube adapted to deliver the input powder to the rotatable holder;
    at least one ultrasonic transducer suspended above and adjacent to the rotatable holder, configured to create a standing wave pattern to levitate and suspend particles of the input powder on the rotatable holder as it passes the at least one ultrasonic transducer, thereby forming a cloud of aerosol particles in the space between the rotatable holder and the at least one ultrasonic transducer; and
    a tube with an inlet end proximate the cloud of aerosol particles and configured to extract particles from said cloud.

2. The system of claim 1, wherein the tube is a probe tube.

3. The system of claim 1, wherein the tube directs the suspended particles to a de-agglomeration system.

4. The system of claim 1, wherein the tube directs the suspended particles to an aerosol outlet.

5. The system of claim 1, further comprising a brush attached to the powder feeder.

6. The system of claim 1, further comprising a motor in mechanical connection with the rotatable holder.

7. The system of claim 1, wherein the rotatable holder comprises a rotary disk or round rotary table.

8. The system of claim 7, further comprising a continuous circular groove in a surface of the rotary disk or round rotary table.

9. The system of claim 1, further comprising a funnel attached to an end of the powder feeder tube, one or more agitators, and one or more mesh strainers.

10. The system of claim 1, further comprising a housing encompassing the rotatable holder, and a gas inlet configured to introduce a gas into the housing.

11. A method of preparing dry powders for dispersion, comprising:
    placing an input powder into a powder feeder;
    directing the input powder to a rotating disc or holder; and
    subjecting the input powder to ultrasonic excitation, wherein the ultrasonic excitation suspends the input powder in a cloud of aerosol particles above the rotating disc.

12. The method of claim 11, further comprising the step of collecting the suspended input powder for de-agglomeration.

13. The method of claim 11, further comprising the steps of:
    introducing gas; and
    removing the suspended input powder and gas.

14. An adapter for off-the-shelf powder dispersers, comprising:
    an ultrasonic transducer configured to fit within an existing off-the-shelf powder disperser comprising a rotary table, wherein the ultrasonic transducer is suspended above the rotary table, wherein the ultrasonic transducer is further configured to create a standing wave for aerial suspension of an input powder as it passes underneath the ultrasonic transducer, thereby forming a cloud of aerosol particles in the space underneath the ultrasonic transducer in preparation for collection of particles from the cloud and subsequent processing or use thereof.

* * * * *